US008768463B2

(12) United States Patent
Anderson et al.

(10) Patent No.: US 8,768,463 B2
(45) Date of Patent: Jul. 1, 2014

(54) METHOD OF DEFINING CONTINUOUS HEART RATE VS AV DELAY VALUES AND SENSED TO PACED AV DELAY OFFSET IN PATIENTS UNDERGOING CARDIAC RESYNCHRONIZATION THERAPY

(75) Inventors: Stephen T. Anderson, North Oaks, MN (US); Dean J. MacCarter, Englewood, CO (US)

(73) Assignee: Shape Medical Systems, Inc., St. Paul, MN (US)

( * ) Notice: Subject to any disclaimer, the term of this patent is extended or adjusted under 35 U.S.C. 154(b) by 489 days.

(21) Appl. No.: 12/944,001

(22) Filed: Nov. 11, 2010

(65) Prior Publication Data

US 2012/0123493 A1     May 17, 2012

(51) Int. Cl.
*A61N 1/37*     (2006.01)

(52) U.S. Cl.
USPC ............................................. 607/17

(58) Field of Classification Search
USPC ............................................. 607/17
See application file for complete search history.

(56) References Cited

U.S. PATENT DOCUMENTS

| | | | |
|---|---|---|---|
| 6,961,616 B2 | 11/2005 | Kramer et al. | |
| 7,225,022 B2 | 5/2007 | Anderson et al. | |
| 2011/0029034 A1* | 2/2011 | Fischer et al. | 607/17 |

OTHER PUBLICATIONS

Nakamoto et al, Japanese Journal of Physiology, *Beat-to-Beat Modulation of Atrioventricular Conduction During Dynamic Exercise in Humans*, vol. 55, 2005, pp. 37-51.

* cited by examiner

*Primary Examiner* — Amanda Patton
(74) *Attorney, Agent, or Firm* — C. G. Mersereau; Nikolai & Mersereau, P.A.

(57) ABSTRACT

A method of data management for optimizing the patient outcome from the provision of cardiac resynchronization therapy (CRT) is described. A regression equation is constructed using 3 data points on a plot of AV delay vs. HR. The x-axis consist of the three points consist of resting HR, HR at the optimal AV delay value during light exercise, and the upper tracking or paced HR. The y-values associated with the three points consist of the AV delay values computed using an equation for ventricular filling time and the optimally determined AV delay value. Also described is a process for determining the sensed to paced AV delay offset. The combined processes yield 4 (the three constant values in the polynomial regression equation $Y=b_2X^2+b_1X+a$ and the sensed to paced AV delay offset) which can be stored on the patient's pacemaker for determining dynamically the AV delay value which is physiologically fine-tuned for each patient from resting HR to the upper tracking or paced HR. In combination with visual observation and computer-assisted ranking of the dependent variables, a physician can utilize the resulting information to render decisions on the optimal choice of the programming biventricular pacemakers/ICDs and DDDR pacemakers for individual patients.

12 Claims, 9 Drawing Sheets

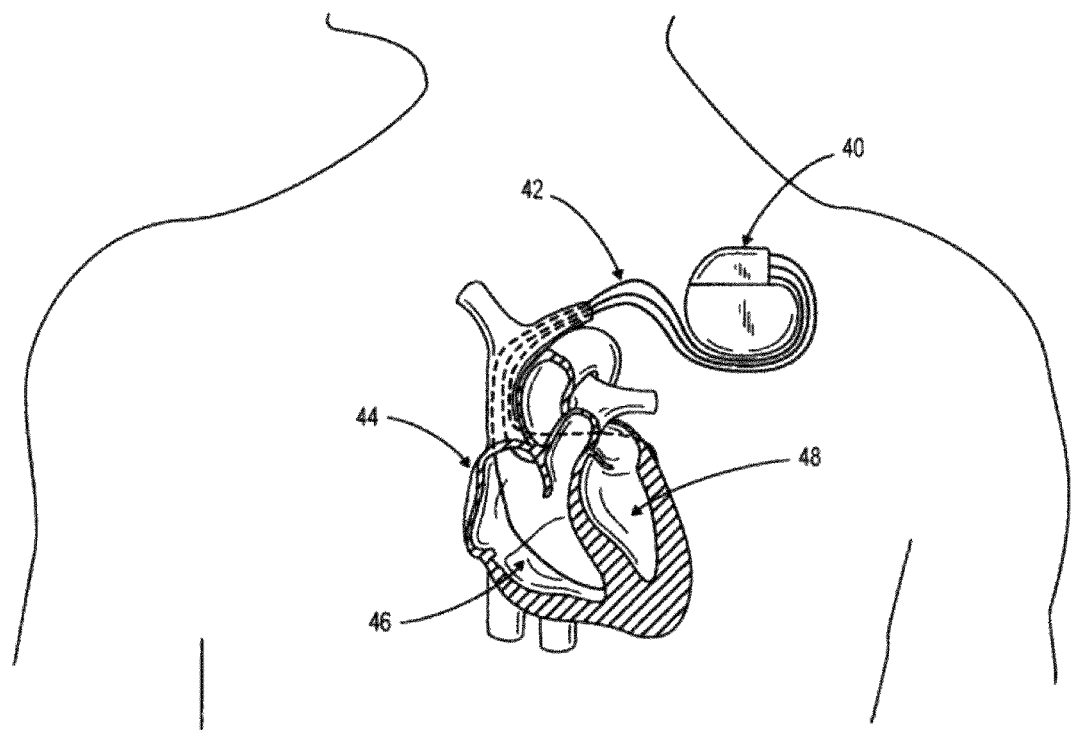
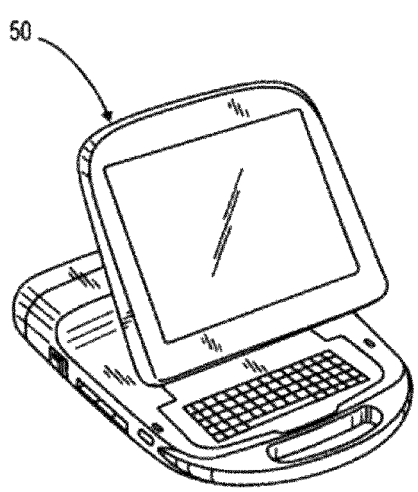
FIG. 2

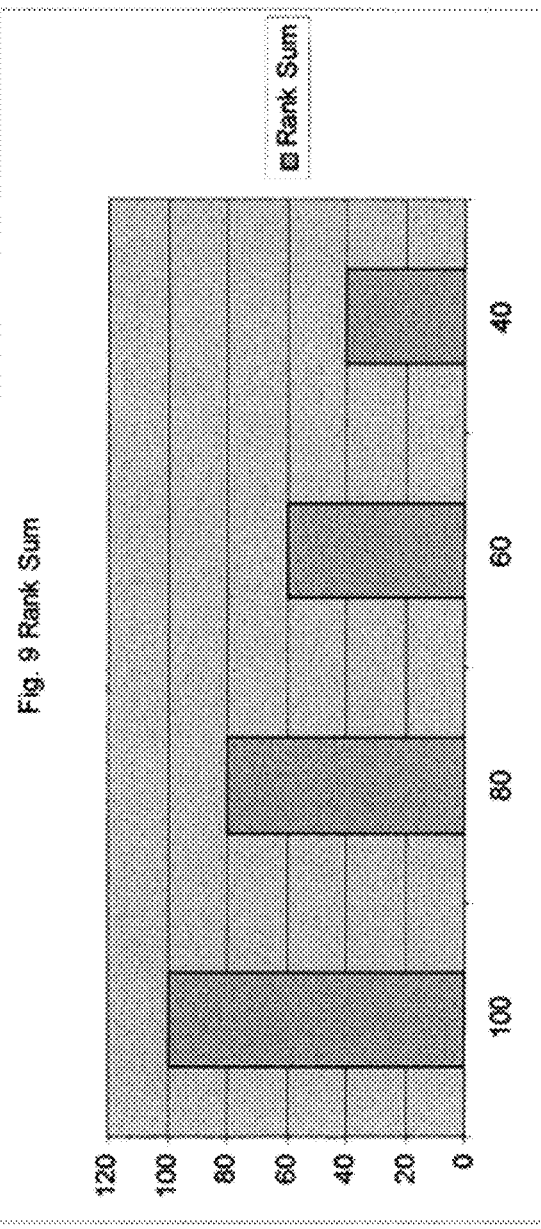

METHOD OF DEFINING CONTINUOUS HEART RATE VS AV DELAY VALUES AND SENSED TO PACED AV DELAY OFFSET IN PATIENTS UNDERGOING CARDIAC RESYNCHRONIZATION THERAPY

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

I. Field of the Invention

The present invention relates generally to the field of cardiac resynchronization therapy (CRT), and more specifically, to a physiologic method for determining optimal atrioventricular (AV) delay values over a range of heart rates from rest to the upper tracking or paced heart rate (HR) and for determining the sensed to paced AV delay offset for optimizing the patient outcome from such therapy. The disclosed method enables physicians to improve the process of programming biventricular pacemakers/ICDs and DDDR pacemakers.

II. Related Art

Several pacemaker manufacturers have the capability of programming a dynamic or auto-decrementing AV delay which decreases linearly from the resting programmed heart rate to the upper tracking or paced HR. The decrement range is not physiologically based upon required left ventricle (LV) filling times or a mid-point AV delay between the lower and upper pacemaker rates which is shown to be the most effective in terms of combined cardiac pump function and breathing efficiency.

The status of the clinical use of a dynamic AV delay is that it has been met with reluctance by the follow-up physician since there is presently no way to assign an adequate resting AV delay. All too often, the dynamic AV delay is set too aggressively based on the use of a linear function which shortens the time at the upper rate excessively. In doing so, ventricular filling and stroke volume output of the heart is compromised, and gas exchange in the lungs and breathing efficiency are adversely affected. The scientific literature has noted that AV conduction times vary inversely to fluctuation of atrial excitement rhythm (Beat-to-beat Modulation of Atrioventricular Conduction During Dynamic Exercise in Humans, Nakamoto, et al, Japanese Journal of Physiology Vol. 55, 37-51, 2005). The cited article also describes this relationship as curvilinear rather than straight line.

In addition to the above, there is no physiologic method other than a pacemaker programmer and an electrically based intra-cardiac electrogram (IECG) technique to estimate the correct AV sensed to paced offset for a cardiac resynchronization therapy (CRT) patient experiencing both sensed and paced atrial activity via the device's data logger. The electrophysiologist typically guesses at whether the optimal AV sensed/paced offset is 30 msec, 45 msec or 50 to 60 msec. It is known that paced conduction time to the left ventricle takes longer since the conduction pulse travels more slowly through atrial/ventricular muscle tissue vs. specialized conducting tissue, as with a paced atrial beat from the atrial appendage or lateral RA vs. an intrinsic atrial beat originating from the sinus node.

Regarding the programming of the upper tracking or paced HR, the only means to select the HR is by "x" percent of the patient's age predicted max HR, the level of patient activity or whether they have ischemic heart disease. Upper tracking or paced HR can range from 110 to 150 bpm, depending on the above criteria and other programmed timing intervals such as the post ventricular atrial refractory period (PVARP).

U.S. Pat. No. 7,225,022, "Method for Optimizing Patient Outcome from Cardiac Resynchronization Therapy", of common inventorship as the present application, discloses a method for determining the optimal AV and VV delay interval using "variables indicative of one or more functions selected from the group consisting of forward pump function (stroke volume output) and retrograde effects of filing pressures, pulmonary venous flow, and gas exchange at the alveolar/capillary membrane interface during exercise". That patent also discloses a method in which a single set of equipment is utilized to optimize all phases/aspects of cardiac resynchronization therapy, including appropriate rate response during exercise/activity and device programming, including dynamic AV and VV delay of which resting AV and VV delay are a portion. Accordingly, the above-referenced patent is deemed incorporated herein by reference in its entirety for any purpose. In the present application, a novel method for determining dynamic AV delay and AV delay offset is disclosed that may be accomplished using a set of equipment such as that used in the above-referenced patent, and as described in FIG. 1.

Definitions of Terms

The following contains definitions and explanations of certain terms as used in the present context.

Upper tracking or paced HR—The programmed Upper tracking or paced Rate is the highest pacing rate at which ventricular tracking of atrial sensed or paced events can occur (in the DDDR, DDD, and VDD modes).

End-Tidal Partial Pressure of $CO_2$ ($PetCO_2$, $ETCO_2$)—The partial pressure of carbon dioxide at the end of expiration, or the highest value of $PCO_2$ during a single expiration.

Forward Pump Function—Refers to the ability of the heart to contract and eject blood which has returned to the heart during its relaxation, or filling, cycle via the aorta against a given amount of resistance, or after load.

Oxygen Pulse ($O_2$ Pulse)—$O_2$ Pulse is an indirect index of combined cardiopulmonary oxygen transport. It is calculated by dividing oxygen uptake (ml/min) by heart rate. In effect, $O_2$ Pulse is equal to the product of stroke volume and arteriovenous $O_2$ difference. Thus circulatory adjustments that occur during exercise, that is, widening arteriovenous $O_2$ difference, increased cardiac output, and redistribution of blood flow to the working muscle, will increase $O_2$ Pulse. Maximal $O_2$ pulse is higher in fitter subjects, lower in the presence of heart disease, and, more importantly, higher at any given workload in the fitter or healthier individual. On the other hand, $O_2$ Pulse will be reduced in any condition that reduces stroke volume . . . " V. Froelicher, J. Myers, et al., Exercise and the Heart. Mosby-Year Book, Inc. 1993, p. 38

Retrograde Pump Function—Refers to the filling of the heart during the relaxation part of the cardiac cycle. Filling pressure and the volume of blood that returns to the heart during diastole are termed preload. Any forward pump failure of the heart can increase the preload on the heart to undesirable levels which, in turn, has an adverse retrograde effect on gas exchange in the lung.

Ventilation-Perfusion Coupling—"For gas exchange to be most efficient, there must be a precise match, or coupling, between ventilation (the amount of gas reaching the alveoli) and perfusion (the blood flow in pulmonary capillaries). Changes in the $PCO_2$ within the alveoli cause changes in the diameters of the bronchioles. Passageways servicing areas where alveolar carbon dioxide levels are high dilate, allowing carbon dioxide to be eliminated from the body more rapidly; those servicing areas where the $PCO_2$ is low constrict. As a result of the modifications these two systems (also for $PO_2$), alveolar ventilation and pulmonary perfusion are always attempting to synchronize. Poor alveolar ventilation results in low oxygen and high carbon dioxide levels in the alveoli; consequently, the pulmonary capillaries constrict and the airways dilate, bringing airflow and blood flow into closer physiological match. High oxygen and low carbon dioxide alveolar partial pressures cause constriction of the respiratory passageways and a flushing of blood into the pulmonary capillaries. At all times, these homeostatic mechanisms provide the most appropriate conditions for efficient gas exchange." E. Marieb, Human Anatomy and Physiology. Benjamin/Cummings Publishing Company, 1992, p. 749

Ventilatory Equivalent for carbon dioxide ($VE/VCO_2$, $EQCO_2$)—The $EQCO_2$ is calculated by dividing ventilation (L/min) by $VCO_2$ (L/min). "$VE/VCO_2$ represents the ventilatory requirement to eliminate a given amount of $CO_2$ produced by the metabolizing tissues. Since metabolic $CO_2$ is a strong stimulus for ventilation during exercise, VE and $VCO_2$ closely mirror one another, and after a drop in early exercise, $VE/VCO_2$ normally does not increase significantly throughout sub-maximal exercise. However, in the presence of chronic heart failure, $VE/VCO_2$ is shifted upward compared to normal, and high $VE/VCO_2$ values are one of the characteristics of the abnormal ventilatory response to exercise in this condition." Ibid Froehlicher.

Estimate of the Drive to breathe (VT/Ti)—Tidal volume is the volume of an average breath; inspiratory time is the average time it takes to inspire. The ratio has been used as an index of ventilatory drive (the combined stimulation to breathe).

SUMMARY OF THE INVENTION

The present invention provides a physiologic method for determining optimal AV delay over a range of heart rates from rest to the upper tracking or paced HR and enables determination of sensed to paced AV delay offset for optimizing patient outcome from CRT.

AV Delay vs. HR Determination

A trend line is a curved line that is used when data fluctuates. For the purposes of the present method, the type of trend line used to relate AV delay values to a range of HRs is dictated by the general shape of the naturally occurring relationship as defined in the literature: i.e., it 1) varies inversely, and 2) changes more rapidly at low HR (rest) than high HR (upper tracking or paced HR).

Two candidate regression methods fit this general description—exponential and second order polynomial. For the purpose of describing the present method, a second order polynomial regression will be used. In general, the order of the polynomial can be determined by the number of fluctuations in the data or by how many bends (hills and valleys) appear in the curve. A second order polynomial trend line generally has only one hill or valley—similar to the naturally occurring HR vs. AV delay relationship. A polynomial regression equation has X raised to integer powers such as $X^2$ and $X^3$. A quadratic equation has the form $Y=b_2X^2+b_1X+a$, where a is the Y-intercept and $b_1$ and $b_2$ are constants. An exponential regression equation may have the form $Y=ce^{bx}$ where c and b are constants and e is the natural logarithm base. Graphically, such an equation produces a parabolic curve, which has been determined to be the shape of the normal HR vs. AV delay curve.

In the present method, three points are needed to determine the second order polynomial regression equation resulting from a regression analysis of the three points. Polynomial regression analysis estimates the relationship between variables so that a given variable can be predicted from one or more other variables. The three points are 1) resting heart rate, AV delay at rest; 2) heart rate at the optimal AV delay determined per the method described below, and 3) the upper tracking or paced HR. Points 1 and 3 are determined to preserve ventricular filling and enhance breathing efficiency. Point 2 determines the degree of "bowing" in the regression equation. Point 1 and 3 are determined using the formula as follows:

AV delay=$\{(60,000/HR\times0.5)\times0.75\}\times0.58$ m, whereby the 60000/HR term equals the conversion of HR in bpm to msec as an R to R interval or cycle length; 0.5 is the estimate of total diastolic filling time in the cardiac cycle;

0.75 is the correction/conversion of total diastolic filling time minus the isovolumic phase to active and passive ventricular filling; and 0.58 is the average conversion factor of the PR interval (diastolic filling time) to an AV delay value.

The resting heart rate used for point 1 can be determined during the procedure for obtaining the optimal AV delay value per the method described below. A physician may wish to program an upper tracking or paced HR based upon a percentage of age predicted maximum heart rate (APMHR). The choice of AV delay value at point 3, the shortest R to R interval, is critical to maintain biventricular pacing. In the event bi-ventricular pacing is lost or fusion beats should occur, the AV delay will be automatically shortened 10 msec for reconstruction of the second order polynomial regression equation.

In this manner, a continuous polynomial regression equation can be described, and the constant values of the equation—a, $b_1$, and $b_2$—can be transmitted to the pacemaker for programmatic determination of the AV delay value for any value of heart rate from rest to the upper tracking or paced HR. Also, use of the equation so determined can assure that the resultant curve is bowed through the optimal HR, AV delay point determined to be optimal by the method, as will be described.

Sensed to Paced AV Delay Offset

The determination of the sensed to paced AV delay offset value will be determined in the patient's resting state with the assumption that very small changes occur in conduction velocity between resting and low exercise conditions. It is known that data loggers and histograms in the device store and display average % paced vs. % sensed atrial activity Paced activity indicates inadequate sinus node response during some time of the day. For example atrial pacing may become more apparent during rest or sleep. In the event that paced atrial activity occurs greater than the EP determined amount (2% to 5%) of the time, the polynomial regression equation can be offset by a predetermined number of msec, effectively shifting the polynomial regression equation upwards. In the event the patient returns to atrial sensed activity from atrial paced activity, the polynomial curve will shift downward by the same number of offset msecs.

The offset will be determined using the following protocol. If the patient's pacemaker is atrial sensing, the optimal Sensed to paced AV delay offset will be determined by overdrive pacing the atrium sensed activity plus 5 b/min. higher. For example if the patient's intrinsic sinus or sensed rate is 75 b/min, the overdrive paced rate shall be 80 b/min. While pacing at 80 b/min in a quiet resting sitting position, the sensed AV interval will be increased to 30 msec, 45 msec and 60 msec using 2 minute intervals. The same criteria for determining the optimal AV delay value will used to determine the optimal sensed to paced AV delay offset value in msec.

In the event the patient is pacemaker dependent with <2% atrial sensing, there will be no need to determine an AV delay offset. Conversely, if less than 2% atrial pacing occurs there will be no need to determine an AV delay offset.

The equations and offset value will differ for each patient, reflecting the fact that each patient has unique cardiac and pulmonary function.

BRIEF DESCRIPTION OF THE DRAWINGS

In the drawings:

FIG. 2 is a schematic drawing that illustrates the functional components of a cardiac resynchronization system;

FIG. 9 illustrates a Report Summary in a histogram format for the data used in Table 2.

DETAILED DESCRIPTION

The following detailed description with respect to patient data is intended to be exemplary of a preferred method of utilizing the concepts of the present invention and is not intended to be exhaustive or limiting in any manner with respect to similar methods and additional or other steps which might occur to those skilled in the art. The following description further utilizes illustrative examples, which are believed sufficient to convey an adequate understanding of the broader concepts to those skilled in the art, and exhaustive examples are believed unnecessary.

General Considerations—The present invention is not intended to make decisions, but rather to provide information to guide the decision making process by the physician. In doing so, decisions regarding programming choices (whether one AV delay setting is better than other choices of delay setting) can be made. In some cases, the answer to these questions may be no—there is no clear reason to use one choice over another. Even in this case, the decision making process described in the present invention is an improvement over a process devoid of specific, sensitive data. In the present invention, specificity is provided by a quantitative analysis of response variables that are based upon well known, proven measurements of human physiology.

Figure 1:
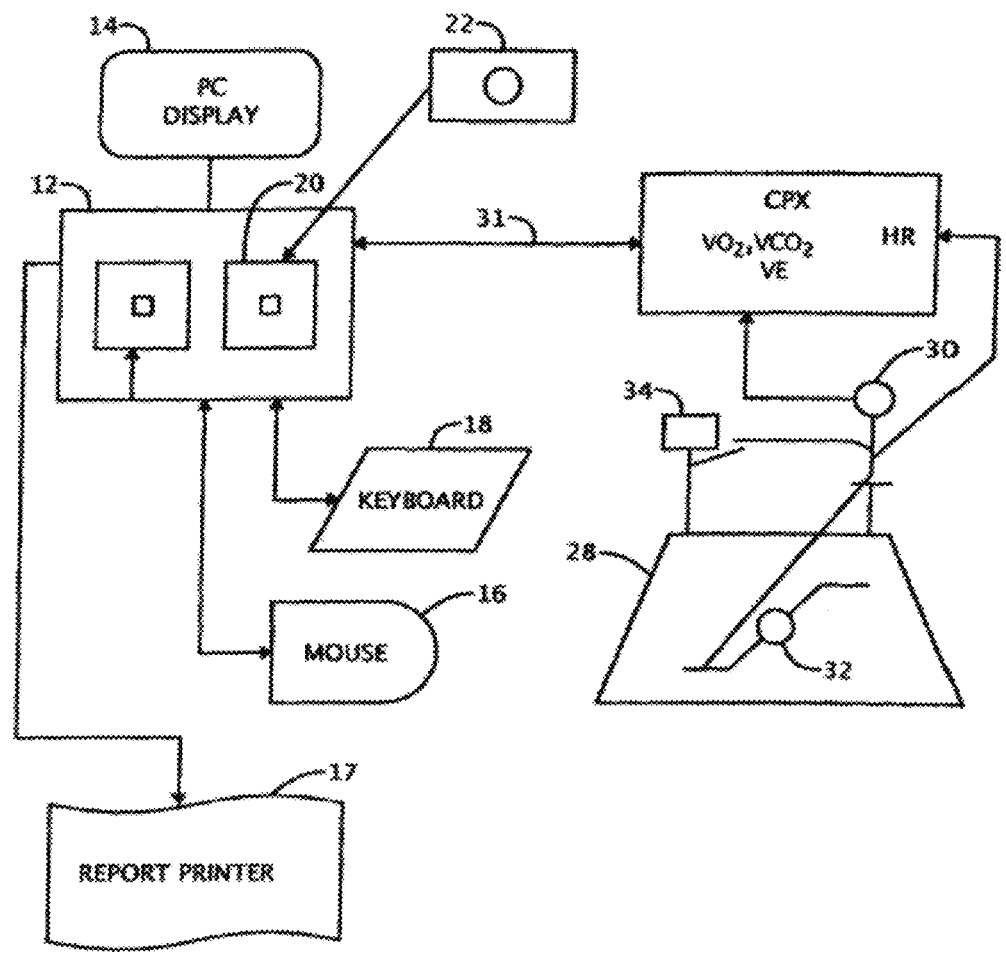
FIG. 1 is a schematic block diagram drawing that illustrates the functional components of a CPX testing system usable with the present invention.

Equipment—With this in mind, typical hardware is shown in FIG. 1, which illustrates typical equipment whereby a cardiopulmonary exercise test (CPX) may be conducted and the results displayed in accordance with the method of the present invention. The system is seen to include a data processing device, here shown as a personal computer or PC 12, which comprises a video display terminal 14 with associated mouse 16, report printer 17 and a keyboard 18. The system further has a floppy disc handler 20 with associated floppy disc 22. As is well known in the art, the floppy-disc handler 20 input/output interfaces comprise read/write devices for reading prerecorded information stored, deleting, adding or changing recorded information, on a machine-readable medium, i.e., a floppy disc, and for providing signals which can be considered as data or operands to be manipulated in accordance with a software program loaded into the RAM or ROM memory (not shown) included in the computing module 12.

The equipment used in the exercise protocol includes either a bicycle ergometer or treadmill designed for use in a cardiopulmonary stress testing system (CPX) as is represented at 28 together with a subject 30 operating a pedal crank input device 32 of the ergometer. A graphic display device 34 interfaces with the subject during operation of the CPX device. The physiological variables may be selected from heart rate (HR), ventilation (VE), rate of oxygen uptake or consumption ($VO_2$) and carbon dioxide production ($VCO_2$) or other variables derived from these basic measurements. Physiological data collected is fed into the computing module 12 via a conductor 31, or other communication device.

The equipment used in cardiac resynchronization therapy is illustrated in FIG. 2, and includes the cardiac resynchronization device (40) and lead system (42). Typically, implantation is done under local anesthesia with the patient sedated. Three leads are implanted: transvenous pacing leads are placed in the right atrium (44) and right ventricle (46), and a third transvenous left ventricle lead (48) is inserted into a distal cardiac vein via the coronary sinus. The goal is to place this third lead on the left ventricular freewall in a mid-cardiac position with good physical and electrical separation from the RV lead. This separation helps to optimize resynchronization to correct the ventricular contraction pattern. Also shown in FIG. 2 is a pacemaker programmer (50), used to program and evaluate the timing characteristics of the pacemaker.

It should be noted that either a PC (12) or pacemaker programmer (50) could be used to acquire the measurements and process those measurements to implement the present invention. Therefore, the further detailed description of the present invention can and will be made independent of the type and characteristics of the data processing means.

Determination of the AV Delay vs. HR Trend Line

Figure 3:
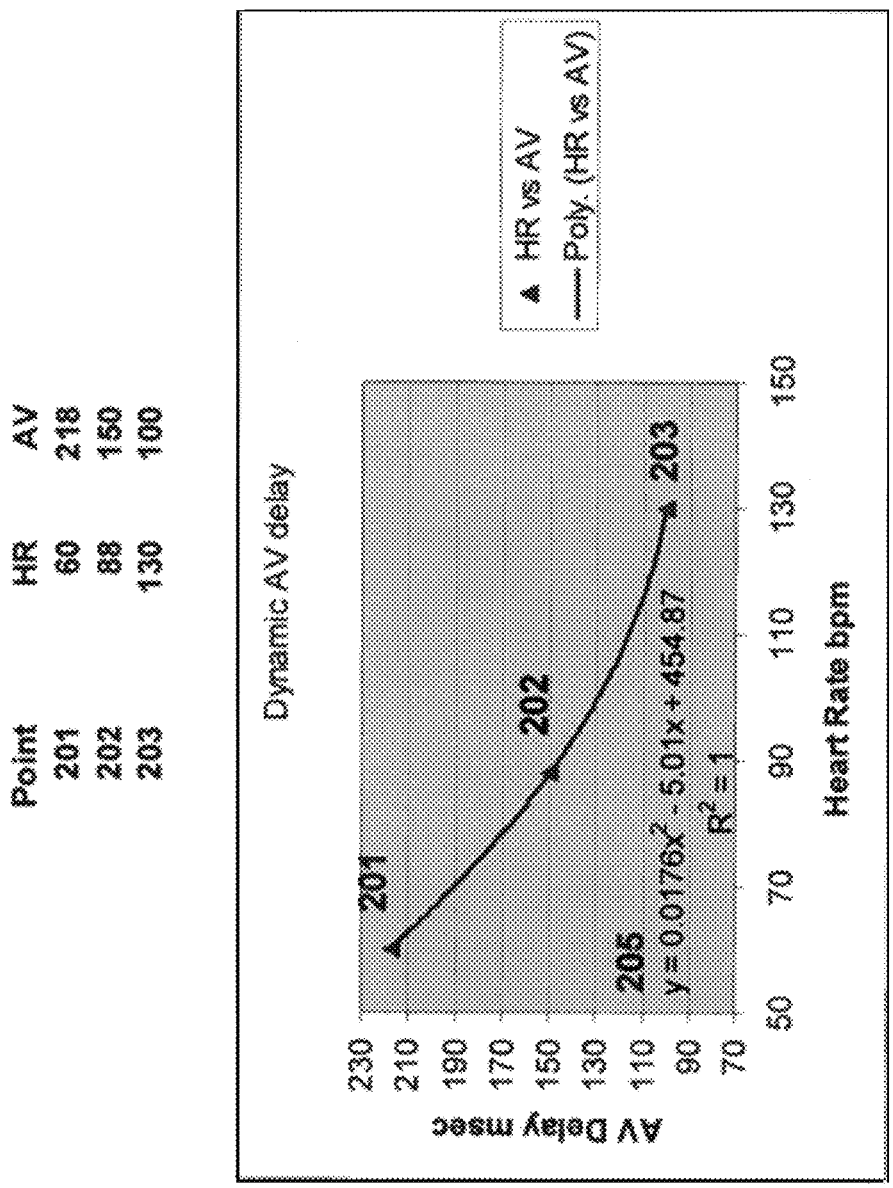
FIG. 3 illustrates a second order polynomial equation and trend line constructed from 3 data points on an AV delay vs. HR plot.

In reference to FIG. 3, three points are defined at 201, 202, and 203. Point 202, optimal AV delay and the HR at optimal AV delay are determined as described in U.S. Pat. No. 7,225,022 and briefly summarized next.

The present invention further provides a computer assisted optimizing process using cardiopulmonary exercise test measurements. Assessment of the most effective AV (paced or sensed) and VV delays is more meaningful when the heart is subjected to an acute change in volume load, as is the case during mild treadmill exercise with an augmented venous return. An "acute assessment" of any combination of AV delay or VV delay that can be programmed is obtained by monitoring of parameters indicative of the patient's "forward" pump function or stroke volume output, as well as "retrograde" effects on filling pressures, pulmonary venous flow, and gas exchange at the alveolar/capillary membrane interface. This acute assessment is performed on the patient during low level (0-2% elevation, 0.8-1.5 miles/hr speed) steady state treadmill exercise. The best choices are ETCO2 for "forward" pump function and $EQCO_2$, as related to inspiratory drive (VT/Ti) for "retrograde" effects. The most optimally programmed AV and interventricular delays will result in the highest expired $ETCO_2$, the lowest VT/Ti, and the lowest $EQCO_2$ during mild, "sub-AT" exercise.

For the purposes of this application, the value of VV delay does not require dynamic adjustment as a function of heart rate because the small range of possible VV delay values, 0-40 ms, is a small percentage of the total R-R cycle length. If the VV delay were to be adjusted between that VV delay determined by the exercise method described herein and the patient's resting HR, an automatic increase of 20% could be programmed to increase the VV delay by only 4 to 8 msec with no change in the VV delay in heart rates between the exercise determined HR and the upper tracking or paced HR. An exercise determined VV interval of 0 msec would have no automatic deviation between rest and upper tracking or paced heart rates.

These parameters are measured at pre-determined values for AV delay and are sequentially programmed into the pacemaker every two minutes. This programming is accomplished manually by placing the programming wand over the implanted device on the patient's chest (or transmitted wirelessly in newer systems) and selecting a delay setting corresponding to each value of AV delay to be considered. All measured data for each breath during the two-minute collection period associated with each of the three delay values is stored into the system database.

Upon completion of each of the two-minute data collection periods, the central tendency of each measured variable is computed for the last 60 seconds of each two minute interval. Such computations of central tendency can include, but is not limited to, the simple arithmetic average, as in Table 1.

TABLE 1

| Variable | Interval 1 | Interval 2 | Interval 3 | Interval 4 |
| --- | --- | --- | --- | --- |
| VE/VCO2 | 41.2 | 43.2 | 62.8 | 60.3 |
| VT/TI | 0.70 | 0.76 | 0.77 | 0.97 |
| PetCO2 | 41.9 | 40.7 | 39.0 | 33.3 |

The Rank value is intended to provide a qualitative assessment of the optimal choice for AV delay. Physiologically, the optimal AV delay value is the value that results in the highest value of ETCO2 and the lowest values for EQCO2 and VT/Ti. Assuming that 4 delay values will be ranked, as in Table 2, the highest average value for $ETCO_2$ is assigned a Rank value of 100, the next highest average value is assigned a Rank value of 80, the next highest average value is assigned a Rank value of 60, and the lowest average value is assigned a Rank value of 40. The lowest average values for $EQCO_2$ and VT/Ti are assigned a Rank value of 100, the next highest average values for each are assigned a Rank value of 80, the next highest average values for each are assigned a Rank value of 60, and the highest average values for each is assigned a Rank value of 40.

The next step is to compute the Average Total Rank. This is done by summing the individually assigned Rank values for each of the variables in the same column and dividing by 3 as in Table 2. The "perfect" Average Rank, then, is 100, which indicates that each variable for that particular setting is in theoretical conformance—the one that should be the highest is the highest and the two that should be the lowest are the lowest for that delay value as seen in FIG. 9.

TABLE 2

| | Rank | | | |
| --- | --- | --- | --- | --- |
| | AV Delay | | | |
| | 100 | 120 | 140 | 160 |
| VE/VCO2 | 100 | 80 | 60 | 40 |
| VT/TI | 100 | 80 | 60 | 40 |
| PetCO2 | 100 | 80 | 60 | 40 |
| Total Rank | 300 | 240 | 180 | 120 |
| Ave Rank | 100 | 80 | 60 | 40 |

In this manner, the AV delay value with the highest Rank and the average steady state heart rate observed during the optimizing protocol are established for point 202.

Figure 4:
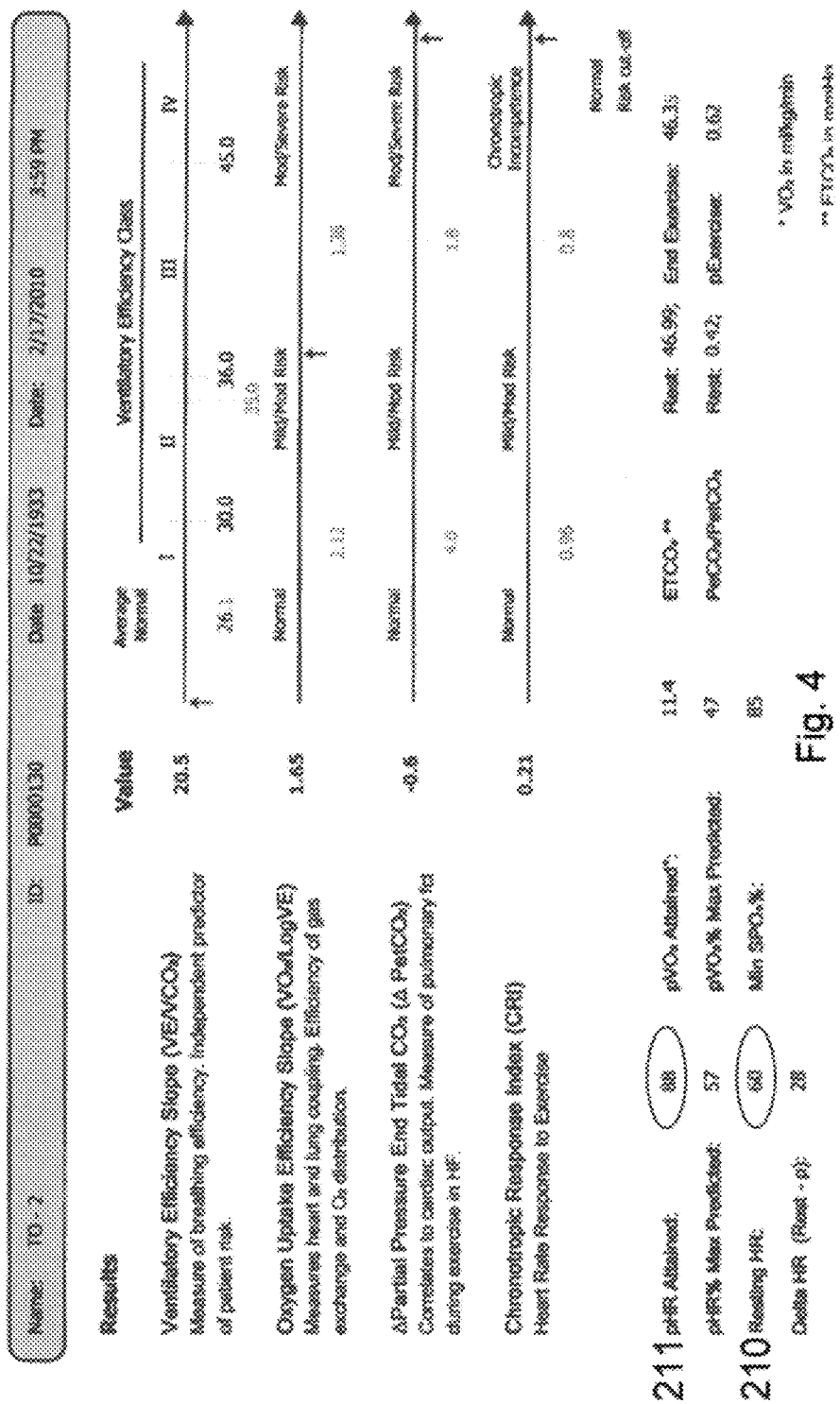
FIG. 4 illustrates therapy optimization report.

Points 201 and 203 are determined by first determining the resting HR and the upper tracking or paced HR from the CRT optimization report, FIG. 4. The resting HR is observed at 210 in FIG. 4, and the HR at which the optimal AV delay was determined is observed at 211 in FIG. 4. In this manner, the resting HR (201) and the upper tracking or paced HR (203) are inserted into the following formula to derive the AV delay for points 201 and 203:

AV delay={(60,000/HR×0.5)×0.75}×0.58 m, whereby the 60000/HR term equals the conversion of HR in bpm to msec as an R to R interval or cycle length;

0.5 is the estimate of total diastolic filling time in the cardiac cycle. The diastolic ratio may also be determined by resting echo during the time of gathering data for CRT implant criteria and may range between 0.5, as mentioned above, to 0.6, thus requiring a slight modification of the above formula;

0.75 is the correction/conversion of total diastolic filling time minus the isovolumic phase to active and passive ventricular filling;

0.58 is the average conversion factor of the PR interval (diastolic filling time) to an AV delay value.

Having determined the values for 201, 202, and 203, the next step is to perform a second order regression analysis (or, optionally, an exponential regression analysis) on these three data points. The analysis yields the equation at 205 in FIG. 3 which is then plotted in relationship to points 201, 202, and 203.

Figure 5:
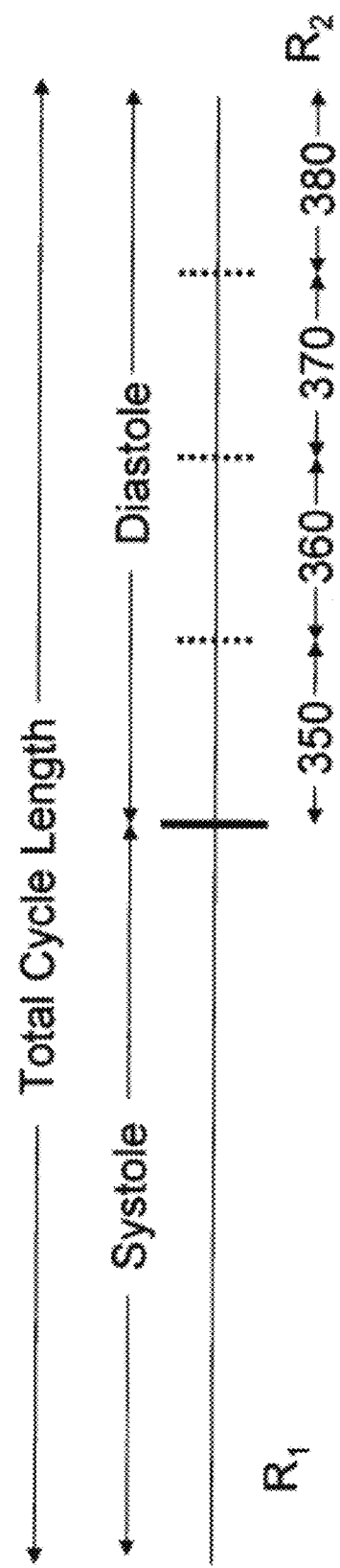
FIG. 5 illustrates a timing diagram for atrial sensing and atrial pacing.

If the patient has been evaluated using tissue Doppler imaging (TDI), the PR interval can be determined by the sum of diastasis (370, FIG. 5) and atrial contraction/filling (380, FIG. 5). This can also be used as an alternative method to determine PR interval or as a check on the formula above for PR interval. If TDI values for 370 and 380 are available, the formula for AV delay values for points 201 and 203 is (diastasis msec+atrial contraction/filling msec)*0.58.

In this manner of determining AV delay values for the range of programmed heart rate, the problem of prematurely stimulating the ventricle and attenuating atrial contribution to filling is avoided.

Determination of Sensed to Paced AV Delay Offset

Figure 6:
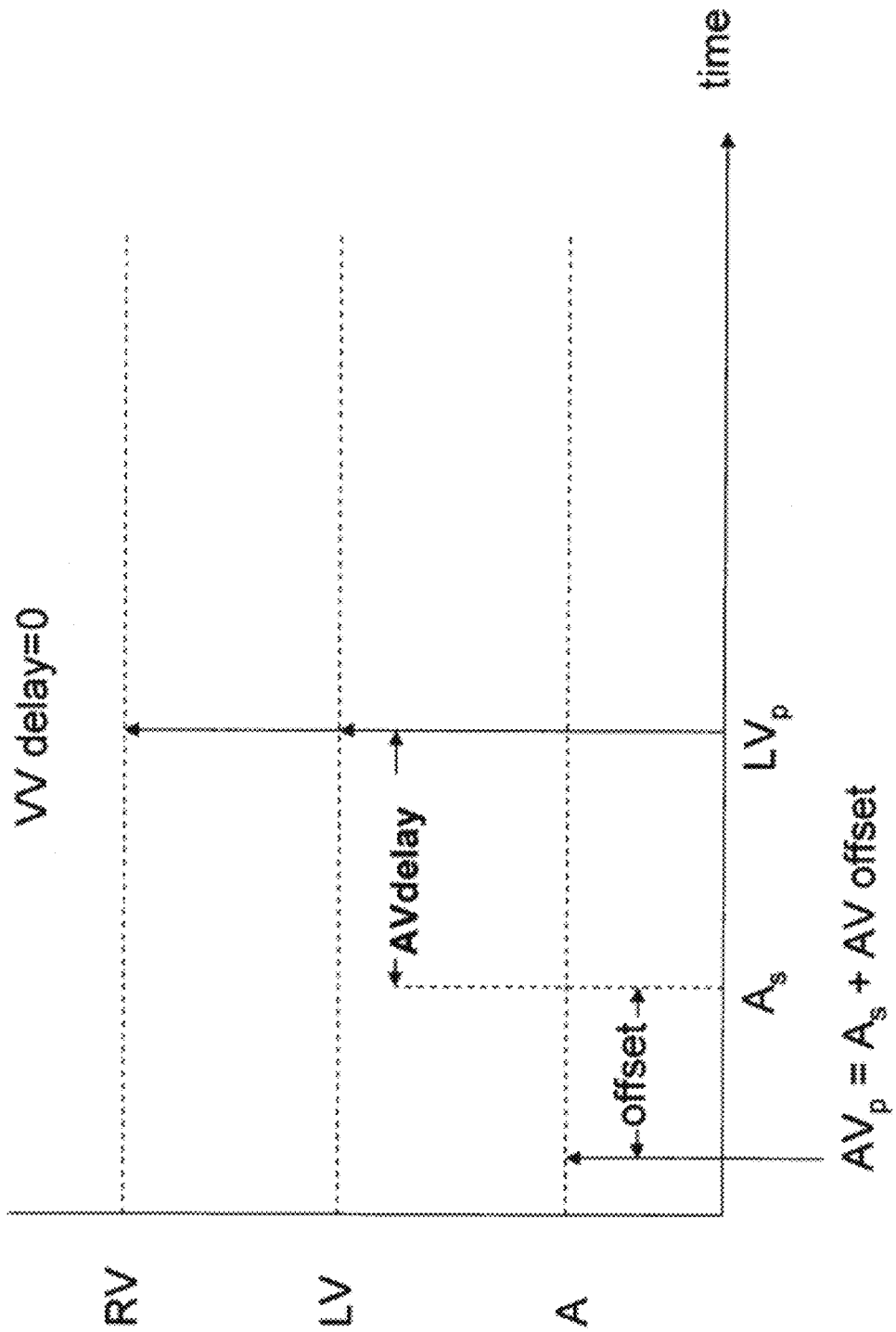
FIG. 6 illustrates protocol for determining the sensed to paced AV delay offset.

FIG. 6 illustrates a timing diagram of a biventricular pacemaker. For normal intrinsic pacing, the patient's natural pacemaker, the sinus node, triggers a pulse to the left ventricle. If the VV delay is programmed to a value of 0, the right ventricle will be pulsed at the same time. The time difference between the two events is the AV delay, or $LV_p(t)-A_s(t)$. If there is no intrinsic pacing (atrial sensed beat followed by biventricular pacing), atrial pacing is necessary. This increases the conduction time and necessitates a longer AV delay ($LV_p-A_s+$ Sensed to paced AV delay offset) than that determined to be optimal for intrinsic pacing (atrial sensed beat followed by biventricular pacing).

Figure 7:
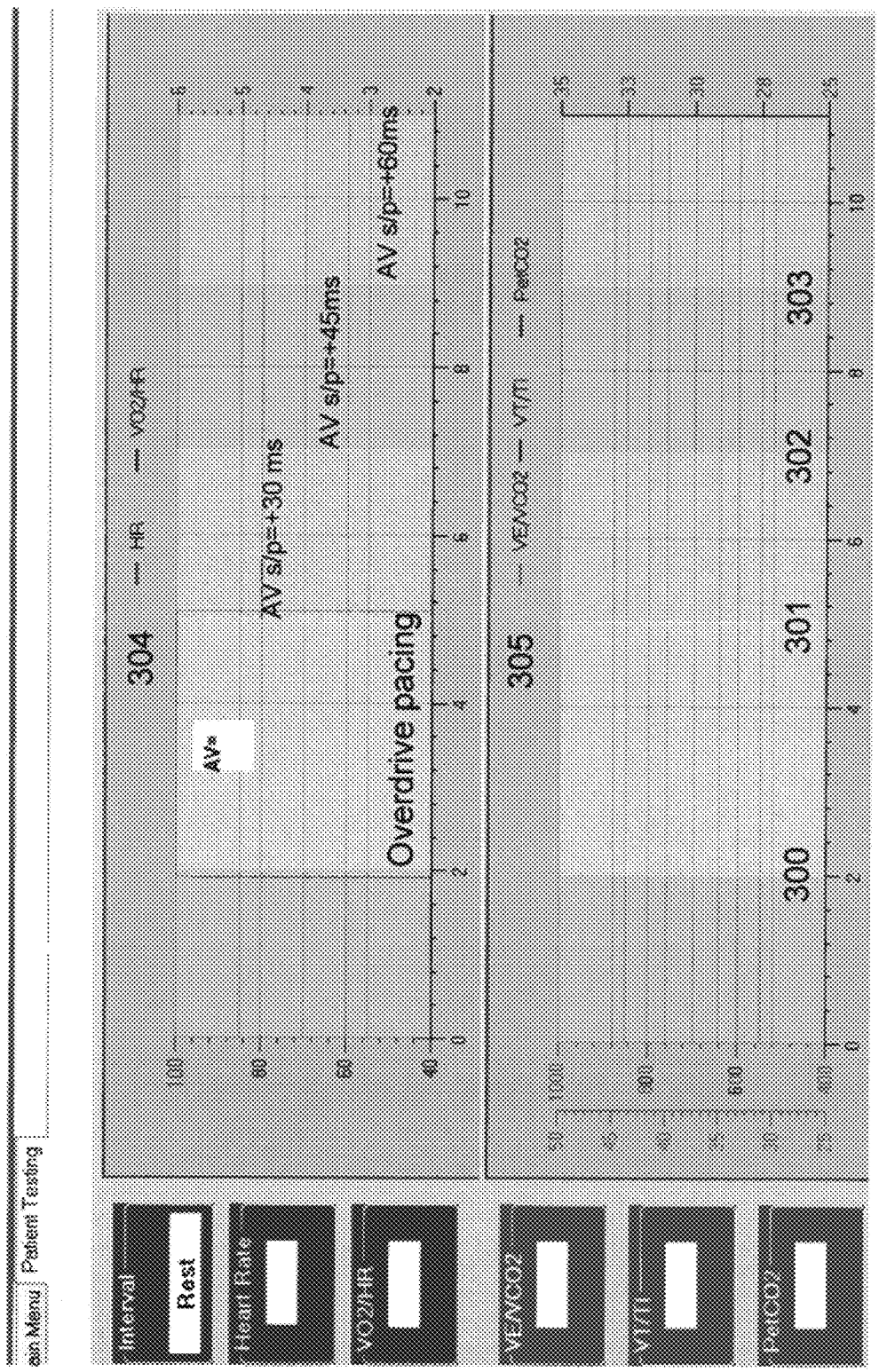
FIG. 7 illustrates the effects of a sensed to paced AV delay offset on the curve illustrated in FIG. 3.

The protocol for determining the sensed to paced AV delay offset is illustrated in FIG. 7. The protocol is as follows:
1. The cardiopulmonary gas exchange variables noted at 304 and 305 are measured and stored in the system database during each of the time periods indicated.
2. The patient is seated and breathing normally for the entire data collection protocol.
3. For the first two minutes, the patient's pacemaker remains programmed to the same settings from the previous interrogation and programming session.
4. At 2 minutes into the protocol, at 300, the patient's pacemaker is switched to overdrive pacing, replacing intrinsic pacing with atrial pacing. The following 3 minutes allows the patient to achieve a steady state condition.
5. At 5 minutes into the protocol (301), the patient's pacemaker is programmed to an AV delay value of 30 msec.
6. At 7 minutes into the protocol (302), the patient's pacemaker is programmed to an AV delay value of 45 msec.
7. At 9 minutes into the protocol (303), the patient's pacemaker is programmed to an AV delay value of 60 msec.
8. At the end of the data collection protocol, 11 minutes, the variables at 305 for each of the 3 intervals (steps 5,6,7) are ranked according to the method described above.
9. The AV delay value for the highest ranked interval is then defined as the sensed to paced AV delay offset.

Figure 8:
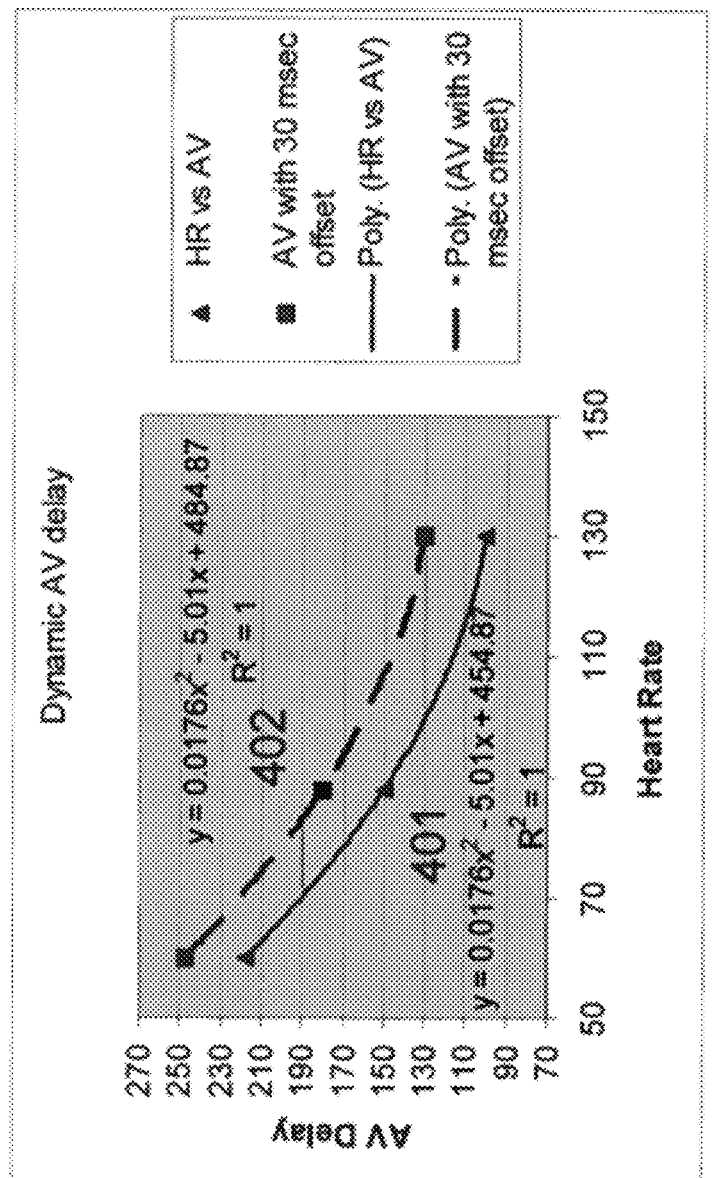
FIG. 8 illustrates the effects of a sensed to paced AV delay offset on the curve illustrated in FIG. 3.

FIG. 8 illustrates the effect of the selected sensed to paced AV delay offset on the second order polynomial regression equation determined as in FIG. 3. As can be seen in FIG. 8, the AV delay vs. HR curve for atrial pacing is shifted upwards by 30 msec (assuming that 30 msec was selected in steps 8 and 9 above) from the atrial sensing curve (401).

In this manner, a physiologically determined AV delay over the range of HR from rest to the upper tracking or paced HR can be characterized by 3 numbers −0.017, −5.01, and 454.87 in FIG. 3 and FIG. 7. When stored on the pacemaker programmer, these values can be transmitted to the patient's pacemaker for computation of the second order polynomial regression equation to adjust the AV delay value in real time as the patient modulates his/her activity. The physiologically determined sensed to paced AV delay offset can also be transmitted to the pacemaker programmer and then to the patient's pacemaker for determining which curve to utilize—intrinsic (401) or paced (402)—to adjust the AV delay value in real time as the patient modulates his/her activity.

The present invention anticipates that the transfer of information between the cardiopulmonary gas exchange system and the pacemaker programming system can occur manually or can occur online via an electronic interface between the two systems.

The invention has been described in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as the equipment details and operating procedures can be accomplished without departing from the scope of the invention itself.

The invention claimed is:

1. A method for defining continuous heart rate vs. AV delay values by defining a regression trend line using three points, the points comprising:
   (a) resting heart rate and AV delay at rest;
   (b) heart rate at optimal AV delay during light exercise;
   (c) upper tracking or paced heart rate and AV delay at upper tracking or paced heart rate;
   communicating said points to a pacemaker programmer for use in programming a pacemaker;
   wherein the AV delay value for points (a) and (c) is determined using an equation for ventricular filling time; and
   wherein the equation for AV delay for points (a) and (c) is AV delay=$\{(60,000/HR \times 0.5) \times 0.75\} \times 0.58$ msec, whereby the 60000/HR term equals the conversion of HR in bpm to msec as an R to R interval or cycle length; 0.5 is the estimate of total diastolic filling time in the cardiac cycle; 0.75 is the correction/conversion of total diastolic filling time minus the isovolumic phase to active and passive ventricular filling; and
   0.58 msec is the average conversion factor of the PR interval (diastolic filling time) to an AV delay value.

2. A method as in claim 1 wherein the optimal AV delay value and associated HR is determined by:
   (a) executing an AV delay optimization protocol defining a time schedule for system operator tasks and data processing tasks for each unique value of AV delay as defined in a boundary condition table unique to a pacemaker manufacturer of interest;
   (b) storing variable values measured for each breath during the delay optimization protocol into a stored data sets table for subsequent analysis;
   (c) computing and storing a central tendency for each measured variable in each data set obtained immediately after collection into an Intermediate table for subsequent analysis;
   (d) computing and storing into a Decision Matrix ranking values for quantifying the response to changes in AV delay settings using the values obtained in (c);
   (e) printing a report of the Decision Matrix with all values used to compute average rank in (d);
   (f) printing a graphical report in the form of a histogram representing the ranking values determined in (d); and
   (g) using an AV delay value that provides the best forward pump function and the best retrograde effect on filling pressures, pulmonary venous flow, and gas exchange at the alveolar/capillary membrane interface using quantitative and qualitative data computed in (a) through (f).

3. A method as in claim 1 wherein said regression trend line through the three points is fit:
   (a) using a second order polynomial regression equation of the form $Y=b_2X^2+b_1X+a$, wherein a is the Y intercept and $b_1$ and $b_2$ are constants; or
   (b) using an exponential regression equation of the form $Y=ce^{bx}$, wherein c and b are constants and e is the base of the natural logarithm.

4. A method as in claim 3 including transmitting the constant terms of the regression equation to a pacemaker programmer and then to a patient's pacemaker.

5. A method as in claim 1 wherein said regression line through the three points is fit:
   (a) using a second order polynomial regression equation of the form $Y=b_2X^2+b_1X+a$, wherein a is the Y intercept and $b_1$ and $b_2$ are constants; or (b) using an exponential regression equation of the form $Y=ce^{bx}$;

(c) determining a sensed to paced AV delay offset in a patient comprising:
  (1) collecting cardiopulmonary gas exchange data according to a cardiopulmonary optimization protocol;
  (2) switching the patient to overdrive atrial pacing;
  (3) changing the AV delay value sequentially to 30 msec, 45 msec, and 60 msec; and
  (4) determining the optimal AV delay value as the highest ranked value according to the following method:
    (i) executing an AV delay optimization protocol defining a time schedule for system operator tasks and data processing tasks for each unique value of AV delay as defined in a boundary condition table unique to a pacemaker manufacturer of interest;
    (ii) storing variable values measured for each breath during the delay optimization protocol into a stored data sets table for subsequent analysis;
    (iii) computing and storing a central tendency for each measured variable in each data set obtained immediately after collection into an Intermediate table for subsequent analysis;
    (iv) computing and storing into a Decision Matrix ranking values for quantifying the response to changes in AV delay settings using the values obtained in (c);
    (v) printing a report of the Decision Matrix with all values used to compute average rank in (d);
    (vi) printing a graphical report in the form of a histogram representing the ranking values determined in (d); and
    (vii) using an AV delay value that provides the best forward pump function and the best retrograde effect on filling pressures, pulmonary venous flow, and gas exchange at the alveolar/capillary membrane interface using quantitative and qualitative data computed in (a) through (f).

6. A method as in claim 5 wherein the values as in (a), (b) and (c) are used in the patient's pacemaker to compute the value of AV delay using the regression equation to program the AV delay value at the heart rate observed at any point in time.

7. A method as in claim 6 including collecting required pacing information via an on-line interface to a pacemaker programmer for entry into the database of the cardiopulmonary gas exchange measurement system for implementation of the method.

8. A method for collecting required pacing information as in claim 1 including manually entering the pacing information into the database of the cardiopulmonary gas exchange measurement system for implementation of the method.

9. A method as in claim 1 wherein AV delay values further take into account tissue Doppler imaging data.

10. A method for determining a sensed to paced AV delay offset in a patient comprising:
  (a) collecting cardiopulmonary gas exchange data according to a cardiopulmonary optimization protocol;
  (b) switching the patient to overdrive atrial pacing;
  (c) changing the AV delay value sequentially to 30 msec, 45 msec, and 60 msec; and
  (d) determining the optimal AV delay value as the highest ranked value according to the following method:
    (1) executing an AV delay optimization protocol defining a time schedule for system operator tasks and data processing tasks for each unique value of AV delay as defined in a boundary condition table unique to a pacemaker manufacturer of interest;
    (2) storing variable values measured for each breath during the delay optimization protocol into a stored data sets table for subsequent analysis;
    (3) computing and storing a central tendency for each measured variable in each data set obtained immediately after collection into an Intermediate table for subsequent analysis;
    (4) computing and storing into a Decision Matrix ranking values for quantifying the response to changes in AV delay settings using the values obtained in (c);
    (5) printing a report of the Decision Matrix with all values used to compute average rank in (d);
    (6) printing a graphical report in the form of a histogram representing the ranking values determined in (d); and
    (7) using an AV delay value that provides the best forward pump function and the best retrograde effect on filling pressures, pulmonary venous flow, and gas exchange at the alveolar/capillary membrane interface using quantitative and qualitative data computed in (a) through (f).

11. A method as in claim 10 including transmitting the sensed to paced AV delay offset to a pacemaker programmer and then to a patient's pacemaker.

12. A pacemaker having a programmed heart rate vs. AV delay relation defined by a regression trend line using three points, the points comprising:
  (a) resting heart rate and AV delay at rest;
  (b) heart rate at optimal AV delay during light exercise; and
  (c) upper tracking or paced heart rate and AV delay at upper tracking or paced heart rate; and
wherein said regression trend line through the three points is fit;
  (1) using a second order polynomial regression equation of the form $Y=b_2X^2+b_1X+a$, wherein a is the Y intercept and $b_1$ and $b_2$ are constants; or
  (2) using an exponential regression equation of the form $Y=ce^{bx}$.

* * * * *